US00PP29430P3

(12) United States Plant Patent
van Rijn

(10) Patent No.: US PP29,430 P3
(45) Date of Patent: Jun. 26, 2018

(54) ***ANTHURIUM* PLANT NAMED 'ARAANTRED3'**

(50) Latin Name: *Anthurium andraeanum*
Varietal Denomination: ARAANTRED3

(71) Applicant: J&D Horticulture B.V., De Lier (NL)

(72) Inventor: Silvia van Rijn, De Lier (NL)

(73) Assignee: J&D Horticulture B.V., De Lier (NL)

( * ) Notice: Subject to any disclaimer, the term of this patent is extended or adjusted under 35 U.S.C. 154(b) by 0 days. days.

(21) Appl. No.: 15/530,817

(22) Filed: Mar. 3, 2017

(65) Prior Publication Data

US 2017/0265368 P1 Sep. 14, 2017

(30) Foreign Application Priority Data

Mar. 10, 2016 (QZ) ..... PBR 2016/0702

(51) Int. Cl.
*A01H 5/02* (2018.01)

(52) U.S. Cl.
USPC ..... Plt./365

(58) Field of Classification Search
USPC ..... Plt./365
CPC ..... A01H 5/02; A01H 5/00; A01H 5/12
See application file for complete search history.

*Primary Examiner* — June Hwu
(74) *Attorney, Agent, or Firm* — Samuel R. McCoy, Jr.

(57) ABSTRACT

'ARAANTRED3' is a new and distinctive variety of *Anthurium* which is characterized by the combination of a bright red cordate spathe with an upright attitude, a generally white spadix, dark green and glossy foliage with an upright attitude, and the stability of all characteristics from generation to generation. The new variety is typically produced as an indoor ornamental plant.

3 Drawing Sheets

Latin name of the genus and species: The Latin name of the genus and species of the novel variety disclosed herein is *Anthurium andraeanum* Linden ex Andre.

Variety denomination: The inventive variety of *Anthurium* disclosed herein has been given the variety denomination 'ARAANTRED3'.

CROSS REFERENCE TO RELATED APPLICATIONS

This application claims priority to the Community Plant Variety Rights application number 2016/0702, filed Mar. 10, 2016, which is herein incorporated by reference.

BACKGROUND OF THE INVENTION

Parentage: The new cultivar is a seedling selection which resulted from the controlled pollination of *Anthurium andraeanum* 'K1', the seed parent, and *Anthurium andraeanum* 'K66', the pollen parent. Both parents are developed and owned by the inventor and were never commercially released. Said cross was performed by the inventor in De Lier, The Netherlands, in May of 2013. Seeds were harvested from 'K1', sown, and grown to maturity in order to evaluate for unique characteristics which may be of commercial value. In August of 2014, after evaluating the seedlings for approximately one and a half years, one progeny was observed to exhibit good plant vigor and a bright red spathe held upright and partially surrounding the spadix. In October of 2014, after further evaluation to confirm the unique characteristics, the new cultivar was selected for commercialization and given the breeder denomination 'ARAANTRED3'.

Asexual Reproduction: Asexual reproduction of 'ARAANTRED3', by way of meristematic tissue culture, was first performed in October of 2014 at a laboratory in De Lier, the Netherlands. Four successive generations so produced have shown that the unique features of the instant cultivar are stable and reproduced true to type.

SUMMARY OF THE INVENTION

The cultivar 'ARAANTRED3' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Anthurium* cultivar 'ARAANTRED3'. These traits, in combination, distinguish 'ARAANTRED3' as a new and distinct cultivar.

1. *Anthurium* 'ARAANTRED3' is a robust, moderately vigor herbaceous perennial with a broad, upright growth habit; and
2. *Anthurium* 'ARAANTRED3' exhibits cordate leaves which are dark green and glossy; and
3. *Anthurium* 'ARAANTRED3' exhibits leaves with an upright attitude; and
4. *Anthurium* 'ARAANTRED3' exhibits a vibrant red spathe with an upright attitude; and
5. *Anthurium* 'ARAANTRED3' exhibits a spathe that maintains its vibrant red color for a relatively long period of time before fading.

Figure 1:
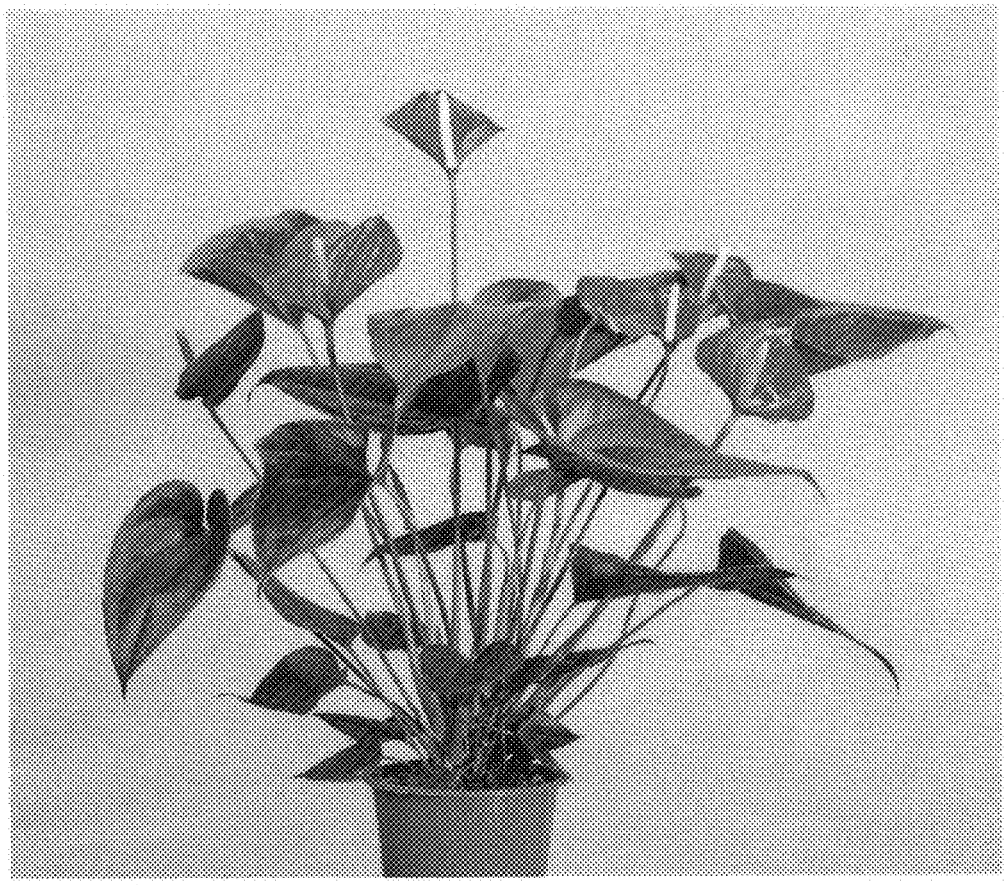
FIG. 1 shows, as nearly true as it is reasonably possible to make the same in color illustrations of this type, an exemplary plant of 'ARAANTRED3', grown in a greenhouse in De Lier, the Netherlands. The plant shown is approximately 7 month old from a rooted cutting, potted into a 14 cm nursery pot.
Figure 2:
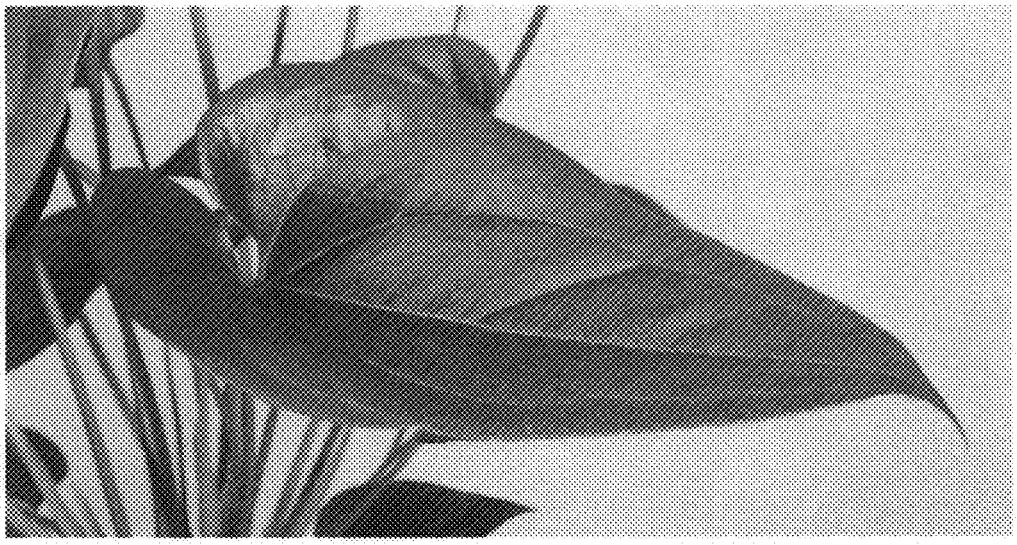
FIG. 2 shows, as nearly true as it is reasonably possible to make the same in color illustrations of this type, the typical foliage of 'ARAANTRED3'.
Figure 3:
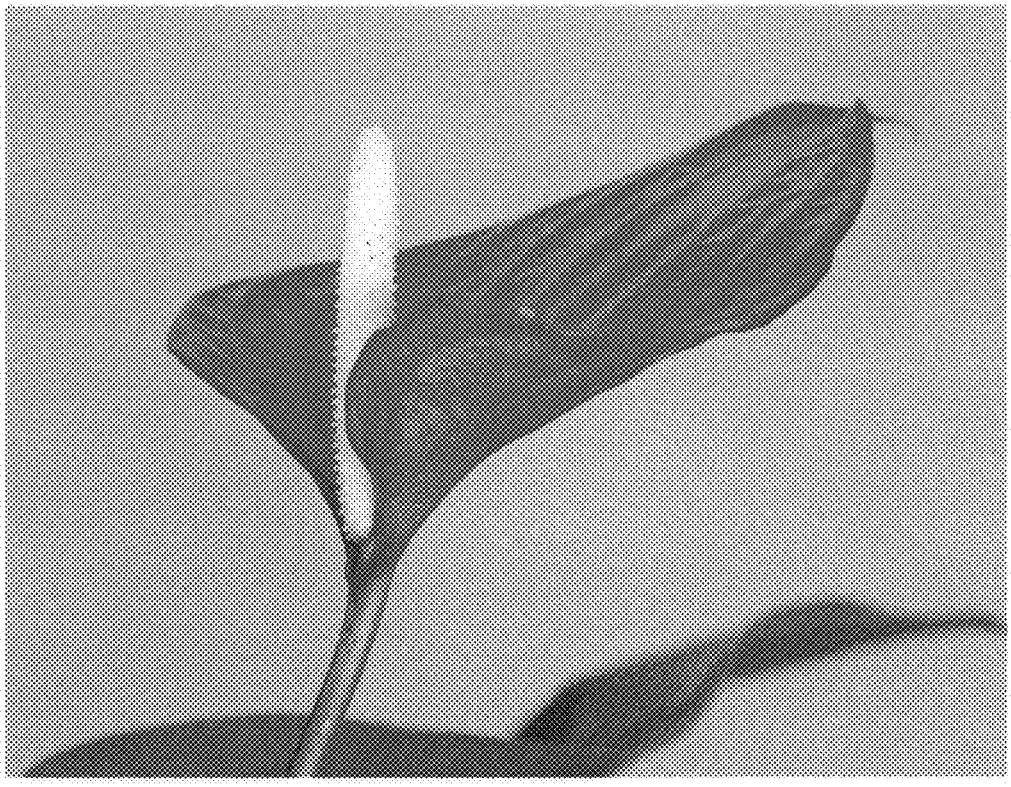
FIG. 3 shows, as nearly true as it is reasonably possible to make the same in color illustrations of this type, the typical inflorescence of 'ARAANTRED3'.

The photographs were taken using conventional techniques and although colors may appear different from actual colors due to light reflectance it is as accurate as possible by conventional photographic techniques.

BOTANICAL DESCRIPTION OF THE PLANT

The following is a detailed botanical description of a new and distinct variety of *Anthurium* known as 'ARAANTRED3', based upon observations made from a sample set of plants grown in 9 cm nursery pots which were approximately one year old from a rooted cutting. Plants were grown in a greenhouse in De Lier, The Netherlands, utilizing conventional greenhouse production protocols for *Anthurium,* which consisted of regular irrigation by way of ebb and flood watering benches and fertilizer applications of a complete fertilizer with micro nutrients at an EC value ranging from 1.0 to 1.8. No chemical pest or disease measures were utilized in production. Young plants are assimilated to the greenhouse under shade cloth and later move to light levels ranging from 3000 to 4000 lux for the final 5 months of production. Observation data was recorded in February of 2017.

Those skilled in the art will appreciate that certain characteristics will vary with older or, conversely, with younger plants. 'ARAANTRED3' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart,* The Royal Horticultural Society, London, sixth edition.

A botanical description of 'ARAANTRED3' and comparisons with the parents and the most similar variety of common knowledge are provided below.

General plant description:

*Growth rate.*—Moderately fast.

*Plant vigor.*—Moderately vigorous.

*Growth habit.*—Clump-forming herbaceous perennial; broad upright.

*Plant shape.*—Broad obovate to globular with flowers sitting above the foliage.

*Height.*—39.0 cm in height, to the highest leaf; 47.5 cm to top of highest flower.

*Width.*—Average 59.0 cm in width.

*Propagation.*—Stem cuttings and meristematic tissue culture.

*Time to initiate roots.*—Approximately 30 days to initiate roots at approximately 23 degrees Centigrade.

*Time to produce a finished marketable plant.*—Approximately 30 to 35 weeks to produce a marketable plant in a 14 cm nursery pot.

*Environmental tolerances.*—Adapt to, at least, USDA Zones 10 to 13 and temperatures ranging from as high as 40 degrees Celsius and as low as 5 degrees Celsius; moderate to high tolerance to rain; low tolerance to wind.

*Pest resistance and susceptibility.*—Plants have not been observed to be susceptible or resistant to pathogens and pests common to *Anthurium.*

Root system:

*Root structure; texture.*—Not very dense; non-fibrous; moderately fleshy.

*Dimensions.*—Average length of 14.0 cm long and 0.3 cm in diameter.

*Color.*—Orange-red, nearest to a combination of RHS 35C and 35D.

Stems:

*Branching characteristics.*—Basally-branched plant with leaves growing in small clumps which form short lateral branches.

*Quantity of clumps per plant.*—3.

*Quantity of additional clumps per year.*—3.

*Lateral branches.*—Dimensions — 3.4 cm long and 1.2 cm in diameter. Aspect — Approximately 10 degrees from vertical. Cross-section — Round. Texture and luster — Smooth, glabrous, and moderately glossy. Strength — Strong. Color, juvenile — Yellow-green, nearest to RHS 145D. Color, mature — Green, nearest to RHS 143B. Color at internodes — Green, nearest to RHS 143B.

Foliage:

*Arrangement.*—Alternate.

*Division.*—Simple.

*Quantity of leaves per lateral branch.*—6 leaves per clump.

*Leaf shape.*—Cordate.

*Leaf apex.*—Apiculate; curved downward.

*Leaf base.*—Deeply cordate; lobes touching to slightly overlapping.

*Aspect.*—Moderately to strongly concave.

*Leaf length.*—Average 21.2 cm in length.

*Leaf width.*—Average 12.2 cm in width.

*Leaf margin.*—Entire; very slightly undulate.

*Texture and luster, adaxial surface.*—Smooth, glabrous and glossy.

*Texture and luster, abaxial surface.*—Smooth, glabrous and moderately glossy.

*Juvenile color, adaxial surface.*—Yellow-green, in between RHS 152A and 152B.

*Juvenile color, abaxial surface.*—Yellow-green, in between RHS 152A and 152B.

*Mature color, adaxial surface.*—Nearest to a combination of green, RHS 139A, and yellow-green, RHS 147A, but darker.

*Mature color, abaxial surface.*—Nearest to a combination of green, RHS 143A, and yellow-green, RHS 146A.

*Venation.*—Vein pattern — Pinnate. Vein color, adaxial surface — Green, in between RHS 143A and 143B. Vein color, abaxial surface — Yellow-green, nearest to RHS 144A.

*Petiole.*—Length — 23.4 cm, including the geniculum. Width — 0.35 cm. Texture and luster, both surfaces — Smooth, glabrous and glossy. Color, adaxial surface — In between green, RHS 143A, and yellow-green, RHS 146A. Color, abaxial surface —

Green, nearest to RHS 143A. Strength — Very strong. Geniculum — Length — Approximately 2.1 cm. Width — Approximately 0.45 cm. Color — Yellow-green, in between RHS 144A and 144B. Petiole wings — Length — Approximately 2.2 cm. Width — Approximately 0.5 cm. Color — Yellow-green, nearest to RHS 144A. Stipule — Occurrence — A dry stipule is present at the base of each petiole. Shape — Narrow oblong. Apex — Acute. Base — Broad cuneate. Dimensions — 5.4 cm long and 0.7 cm wide. Texture and luster, both surfaces — Smooth, glabrous, and matte. Color, both surfaces — Greyed-orange, in between RHS 165B and 166B.

Inflorescence:

*Type.*—Consisting of a spathe and spadix.

*Arrangement.*—Inflorescences are carried at or slightly above the leaf plane.

*Quantity per clump.*—3.

*Quantity per plant.*—9.

*Natural flowering season.*—Winter into spring.

*Height of spathe.*—5.3 cm.

*Time to flowering.*—13 weeks.

*Fragrance.*—Non fragrant.

*Self-cleaning or persistent.*—Persistent.

*Flower longevity.*—Flowers stay in good condition for approximately 4 weeks.

*Peduncle.*—Cross-section — Elliptical. Attitude — Approximately 20 degrees to the lateral branch axis. Length — Approximately 31.1 cm. Diameter — Approximately 0.4 cm. Texture and luster, both surfaces — Smooth, glabrous, and moderately glossy. Color — Yellow-green, nearest to RHS 146A, and suffused with greyed-orange, nearest to in between RHS 177A and 177B. Strength — Strong.

Spathe:

*Aspect.*—Horizontal; apex pointed downward at approximately 45 degrees from horizontal.

*Length.*—Approximately 10.8 cm.

*Width.*—Approximately 9.7 cm.

*Shape.*—Cordate.

*Aspect.*—Slightly concave.

*Margin.*—Entire; lightly undulated.

*Apex.*—Apiculate.

*Base.*—Cordate.

*Texture and luster, upper surface.*—Smooth, glabrous, and very glossy.

*Texture and luster, lower surface.*—Smooth, glabrous, and very glossy.

*Color.*—Upper surface, when opening — Red, nearest to RHS 46B. Lower surface, when opening — Red, nearest to RHS 48A, and darker towards the apex, in between RHS 50A and 50B. Upper surface, when fully opened — Red, nearest to RHS 45B. Lower surface, when fully opened — Red, nearest to in between RHS 46B and 47B. Venation on the upper surface, when fully opened — Red, nearest to RHS 46A. Venation on the lower surface, when fully opened — Red, nearest to RHS 46A. Upper surface when fading — Greyed-purple, nearest to RHS 183A. Lower surface when fading — Greyed-orange, nearest to RHS N167B, and heavily suffused with yellow-green, nearest to RHS 152A.

Spadix:

*Aspect.*—Approximately 50 degrees to the spathe.

*Shape.*—Cylindrical.

*Apex.*—Obtuse.

*Base.*—Obtuse.

*Length.*—Approximately 5.0 cm.

*Width.*—Approximately 0.8 cm.

*Texture and luster.*—Smooth, glabrous, and matte.

*Color.*—When opening — Yellow, nearest to in between RHS 11C and 11D. When fully opened — Yellow, nearest to RHS 12D at and towards the apex; middle section is lighter, nearest to RHS 11D; yellow towards the base, nearest to RHS 12D. When fading — Green, nearest to RHS 143C; apex is yellow, RHS 11A.

*Quantity of flowers per spadix.*—Approximately 240.

*Spadix flower arrangement.*—Spirally placed on spadix.

*Spadix flower shape.*—Flattened; rotate.

*Spadix flower diameter.*—Approximately 2 mm.

*Spadix flower depth.*—Approximately 0.8 mm.

Reproductive organs:

*Androecium.*—Stamen quantity — 4. Filament — Dimensions — Approximately 0.75 mm long and approximately 0.25 mm in diameter. Color — A combination of light yellow-orange; RHS color designations cannot be determined due to the minute nature of the filament. Anther — Anther shape — Narrow, oblong with a longitudinal slit forming two halves. Anther size — 0.5 mm long and 0.25 mm in diameter. Anther color — Yellow, nearest to RHS 11D. Pollen — Amount of pollen — Scarce. Pollen color — Yellow, nearest to RHS 11D.

*Gynoecium.*—Pistil quantity — One. Length — 0.5 mm. Stigma — Shape — Club-shaped. Dimensions — Approximately 0.3 mm across and 0.15 mm tall. Color — White, nearest to RHS 155C. Style — Length — 0.35 mm. Color — White, nearest to RHS 155C. Ovary — Color — Yellow, nearest to RHS 11D.

Seed and fruit: Seed production has not been observed.

COMPARISONS WITH THE PARENT

Plants of the new cultivar 'ARAANTRED3' differ from the seed parent, *Anthurium* 'K1', in the following characteristics described in Table 1 below.

TABLE 1

| Characteristic | 'ARAANTRED3' | 'K1' |
|---|---|---|
| Leaf size. | Larger than 'K1'. | Smaller than 'ARAANTRED3'. |
| Spadix apex. | Less rounded. | More rounded. |
| General coloration of the spadix. | White. | Greyed-white. |

Plants of the new cultivar 'ARAANTRED3' may be distinguished from the pollen parent, 'K66', by the following combination of characteristics described in Table 2 below.

TABLE 2

| Characteristic | 'ARAANTRED3' | 'K66' |
|---|---|---|
| General coloration of mature foliage. | Darker green. | Lighter green. |

TABLE 2-continued

| Characteristic | 'ARAANTRED3' | 'K66' |
|---|---|---|
| General coloration of the spathe. | More vibrant red. | Less vibrant red. |
| General coloration of the spadix. | White with a yellow apex. | White; apex is white. |

COMPARISONS WITH THE MOST SIMILAR VARIETY OF COMMON KNOWLEDGE

Plants of the new cultivar 'ARAANTRED3' differ from the commercial variety, *Anthurium* 'RYN2007046' (not patented in the United States; Community Plant Variety Rights grant number 32139), in the following characteristics described in Table 3 below.

TABLE 3

| Characteristic | 'ARAANTRED3' | 'RYN2007046' |
|---|---|---|
| Length of pedicel. | Shorter than 'RYN2007046'. | Shorter than 'ARAANTRED3'. |
| Leaf aspect. | Leaf is less concave. | Leaf is more concave. |
| General coloration of the spathe. | More vibrant red. | Less vibrant red. |
| General coloration of the spadix. | White with a yellow apex. | Greyed-white. |
| Spadix apex. | Obtuse. | Narrowly obtuse. |

That which is claimed is:

1. A new and distinct variety of *Anthurium* plant named 'ARAANTRED3', substantially as described and illustrated herein.

* * * * *